(12) United States Patent
Bourne et al.

(10) Patent No.: US 10,398,724 B2
(45) Date of Patent: Sep. 3, 2019

(54) BULKING AGENTS

(71) Applicant: Boston Scientific Scimed, Inc., Maple Grove, MN (US)

(72) Inventors: George Bourne, Southborough, MA (US); Michael Madden, Temple, NH (US); Arthur R. Madenjian, Winchester, MA (US); Doreen Rao, Sudbury, MA (US); Marcia Buiser, South Grafton, MA (US); Jianmin Li, Lexington, MA (US); Raymond Rackley, Shaker Heights, OH (US); Barry N. Gellman, N. Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/082,274

(22) Filed: Nov. 18, 2013

(65) Prior Publication Data

US 2014/0072636 A1 Mar. 13, 2014

Related U.S. Application Data

(62) Division of application No. 13/792,346, filed on Mar. 11, 2013, now Pat. No. 8,586,071, which is a division of application No. 12/946,990, filed on Nov. 16, 2010, now Pat. No. 8,394,400, which is a division of application No. 10/459,895, filed on Jun. 12, 2003, now abandoned.

(60) Provisional application No. 60/388,446, filed on Jun. 12, 2002.

(51) Int. Cl.
| | |
|---|---|
| *A61K 31/765* | (2006.01) |
| *A61L 27/16* | (2006.01) |
| *A61L 27/50* | (2006.01) |
| *A61M 5/31* | (2006.01) |
| *A61K 9/00* | (2006.01) |
| *A61M 25/10* | (2013.01) |

(52) U.S. Cl.
CPC .......... *A61K 31/765* (2013.01); *A61K 9/0024* (2013.01); *A61L 27/16* (2013.01); *A61L 27/50* (2013.01); *A61M 5/31* (2013.01); *A61M 25/1025* (2013.01)

(58) Field of Classification Search
CPC ..... A61K 31/765; A61K 9/0024; A61L 27/16; A61L 27/50; A61M 5/31; A61M 25/1025
See application file for complete search history.

(56) References Cited

U.S. PATENT DOCUMENTS

| | | |
|---|---|---|
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,055,377 A | 10/1977 | Erickson et al. |
| 4,076,640 A | 2/1978 | Forgensi et al. |
| 4,098,728 A | 7/1978 | Rosenblatt |
| 4,110,529 A | 8/1978 | Stoy |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,568,559 A | 2/1986 | Nuwayser et al. |
| 4,573,967 A | 3/1986 | Hargrove et al. |
| 4,622,362 A | 11/1986 | Rembaum |
| 4,623,706 A | 11/1986 | Timm et al. |
| 4,657,756 A | 4/1987 | Rasor et al. |

(Continued)

FOREIGN PATENT DOCUMENTS

| | | |
|---|---|---|
| DE | 100 26 620 A1 | 7/2002 |
| EP | 0251695 | 1/1988 |

(Continued)

OTHER PUBLICATIONS

Horak, Biomaterials, vol. 7, Issue 3, Published 1986, Abstract.*
Walsh et al. (Role of Angiography and Embolization for Massive Gastroduodenal Hemorrhage, Journal of Gastrointestinal Surgery, pp. 61-66, vol. 3, No. 1, published 1999).*
Contigen® Bard® Collagen Implant website, "Contigen® Implant can provide safe, effective treatment when surgery is not the preferred or recommended therapy," http://www.bardcontigen.com/physician.htm, 2 pages, (downloaded Jun. 5, 2002).
PPTI Product Development: Urology Applications website, "Female Stress Urinary Incontinence," http://www.ppti.com/Market/SUI.html, 3 pages, (downloaded Jun. 5, 2002).

(Continued)

*Primary Examiner* — Alma Pipic

(57) ABSTRACT

The invention relates to bulking agents and apparatus and methods for using the disclosed bulking agents. The bulking agents can be used to treat such conditions as urinary and fecal incontinence, gastro-esophageal reflux, aneurismal blockages, and cosmetic deformities. The invention also relates to an injection method that reduces the injection pressure required to place the bulking agents.

20 Claims, 7 Drawing Sheets

(56) References Cited

U.S. PATENT DOCUMENTS

| | | | |
|---|---|---|---|
| 4,661,137 | A | 4/1987 | Garnier et al. |
| 4,663,358 | A | 5/1987 | Hyon et al. |
| 4,671,954 | A | 6/1987 | Goldberg et al. |
| 4,675,113 | A | 6/1987 | Graves et al. |
| 4,678,814 | A | 7/1987 | Rembaum |
| 4,680,320 | A | 7/1987 | Uku et al. |
| 4,681,119 | A | 7/1987 | Rasor et al. |
| 4,742,086 | A | 5/1988 | Masamizu et al. |
| 4,743,507 | A | 5/1988 | Franses et al. |
| 4,772,635 | A | 9/1988 | Mitschker et al. |
| 4,773,393 | A | 9/1988 | Haber et al. |
| 4,782,097 | A | 11/1988 | Jain et al. |
| 4,789,501 | A | 12/1988 | Day et al. |
| 4,795,741 | A | 1/1989 | Leshchiner et al. |
| 4,801,458 | A | 1/1989 | Hidaka et al. |
| 4,804,366 | A | 2/1989 | Zdeb et al. |
| 4,819,637 | A | 4/1989 | Dormandy, Jr. et al. |
| 4,822,535 | A | 4/1989 | Ekman et al. |
| 4,833,237 | A | 5/1989 | Kawamura et al. |
| 4,850,978 | A | 7/1989 | Dudar et al. |
| 4,859,711 | A | 8/1989 | Jain et al. |
| 4,863,972 | A | 9/1989 | Itagaki et al. |
| 4,929,400 | A | 5/1990 | Rembaum et al. |
| 4,933,372 | A | 6/1990 | Feibush et al. |
| 4,954,399 | A | 9/1990 | Tani et al. |
| 4,981,625 | A | 1/1991 | Rhim et al. |
| 4,990,340 | A | 2/1991 | Hidaka et al. |
| 4,999,188 | A | 3/1991 | Solodovnik et al. |
| 5,007,940 | A | 4/1991 | Berg |
| 5,011,677 | A | 4/1991 | Day et al. |
| H915 | H | 5/1991 | Gibbs |
| 5,032,117 | A | 7/1991 | Motta |
| 5,034,324 | A | 7/1991 | Shinozaki et al. |
| 5,047,438 | A | 9/1991 | Feibush et al. |
| 5,079,274 | A | 1/1992 | Schneider et al. |
| 5,106,903 | A | 4/1992 | Vanderhoff et al. |
| 5,114,421 | A | 5/1992 | Polak |
| 5,116,387 | A | 5/1992 | Berg |
| 5,120,349 | A | 6/1992 | Stewart et al. |
| 5,125,892 | A | 6/1992 | Drudik |
| 5,147,631 | A | 9/1992 | Glajch et al. |
| 5,147,937 | A | 9/1992 | Frazza et al. |
| 5,149,543 | A | 9/1992 | Cohen et al. |
| 5,158,573 | A | 10/1992 | Berg |
| 5,171,214 | A | 12/1992 | Kolber et al. |
| 5,190,766 | A | 3/1993 | Ishihara |
| 5,202,352 | A | 4/1993 | Okada et al. |
| 5,216,096 | A | 6/1993 | Hattori et al. |
| 5,253,991 | A | 10/1993 | Yokota et al. |
| 5,260,002 | A | 11/1993 | Wang |
| 5,288,763 | A | 2/1994 | Li et al. |
| 5,292,814 | A | 3/1994 | Bayer et al. |
| 5,302,369 | A | 4/1994 | Day et al. |
| 5,314,974 | A | 5/1994 | Ito et al. |
| 5,316,774 | A | 5/1994 | Eury et al. |
| 5,344,452 | A | 9/1994 | Lemperle |
| 5,344,867 | A | 9/1994 | Morgan et al. |
| 5,354,290 | A | 10/1994 | Gross |
| 5,369,133 | A | 11/1994 | Ihm et al. |
| 5,369,163 | A | 11/1994 | Chiou et al. |
| 5,369,710 | A | 11/1994 | Asai |
| 5,382,260 | A | 1/1995 | Dormandy, Jr. et al. |
| 5,384,124 | A | 1/1995 | Courteille et al. |
| 5,385,561 | A | 1/1995 | Cerny |
| 5,397,303 | A | 3/1995 | Sancoff et al. |
| 5,398,851 | A | 3/1995 | Sancoff et al. |
| 5,403,870 | A | 4/1995 | Gross |
| 5,417,982 | A | 5/1995 | Modi |
| 5,431,174 | A | 7/1995 | Knute |
| 5,435,645 | A | 7/1995 | Faccioli et al. |
| 5,456,693 | A | 10/1995 | Conston et al. |
| 5,468,801 | A | 11/1995 | Antonelli et al. |
| 5,476,472 | A | 12/1995 | Dormandy, Jr. et al. |
| 5,484,584 | A | 1/1996 | Wallace et al. |
| 5,490,984 | A | 2/1996 | Freed |
| 5,494,682 | A | 2/1996 | Cohen et al. |
| 5,494,940 | A | 2/1996 | Unger et al. |
| 5,512,604 | A | 4/1996 | Demopolis |
| 5,514,090 | A | 5/1996 | Kriesel et al. |
| 5,525,334 | A | 6/1996 | Ito et al. |
| 5,534,589 | A | 7/1996 | Hager et al. |
| 5,541,031 | A | 7/1996 | Yamashita et al. |
| 5,542,935 | A | 8/1996 | Unger et al. |
| 5,553,741 | A | 9/1996 | Sancoff et al. |
| 5,556,610 | A | 9/1996 | Yan et al. |
| 5,556,931 | A | 9/1996 | Imura et al. |
| 5,558,255 | A | 9/1996 | Sancoff et al. |
| 5,558,822 | A | 9/1996 | Gitman et al. |
| 5,558,856 | A | 9/1996 | Klaveness et al. |
| 5,559,266 | A | 9/1996 | Klaveness et al. |
| 5,567,415 | A | 10/1996 | Porter |
| 5,569,193 | A | 10/1996 | Hofstetter et al. |
| 5,569,449 | A | 10/1996 | Klaveness et al. |
| 5,569,468 | A | 10/1996 | Modi |
| 5,571,182 | A | 11/1996 | Ersek et al. |
| 5,583,162 | A | 12/1996 | Li et al. |
| 5,585,112 | A | 12/1996 | Unger et al. |
| 5,595,821 | A | 1/1997 | Hager et al. |
| 5,622,657 | A | 4/1997 | Takada et al. |
| 5,635,215 | A | 4/1997 | Takahashi et al. |
| 5,637,087 | A | 6/1997 | O'Neil et al. |
| 5,637,215 | A | 6/1997 | Boschetti et al. |
| 5,639,710 | A | 6/1997 | Lo et al. |
| 5,648,095 | A | 7/1997 | Illum et al. |
| 5,648,100 | A | 7/1997 | Boschetti et al. |
| 5,650,116 | A | 7/1997 | Thompson |
| 5,651,990 | A | 7/1997 | Takada et al. |
| 5,653,922 | A | 8/1997 | Li et al. |
| 5,657,756 | A | 8/1997 | Vrba |
| 5,681,576 | A | 10/1997 | Henry |
| 5,695,480 | A | 12/1997 | Evans et al. |
| 5,695,740 | A | 12/1997 | Porter |
| 5,701,899 | A | 12/1997 | Porter |
| 5,716,981 | A | 2/1998 | Hunter et al. |
| 5,718,884 | A | 2/1998 | Klaveness et al. |
| 5,723,269 | A | 3/1998 | Akagi et al. |
| 5,725,534 | A | 3/1998 | Rasmussen |
| 5,746,734 | A | 5/1998 | Dormandy et al. |
| 5,752,974 | A | 5/1998 | Rhee et al. |
| 5,760,097 | A | 6/1998 | Li et al. |
| 5,766,147 | A | 6/1998 | Sancoff et al. |
| 5,770,222 | A | 6/1998 | Unger et al. |
| 5,779,668 | A | 7/1998 | Grabenkort |
| 5,785,642 | A | 7/1998 | Wallace et al. |
| 5,785,682 | A | 7/1998 | Grabenkort |
| 5,792,478 | A | 8/1998 | Lawin et al. |
| 5,795,562 | A | 8/1998 | Klaveness et al. |
| 5,797,953 | A | 8/1998 | Tekulve |
| 5,807,323 | A | 9/1998 | Kriesel et al. |
| 5,813,411 | A | 9/1998 | Van Bladel et al. |
| 5,823,198 | A | 10/1998 | Jones et al. |
| 5,827,502 | A | 10/1998 | Klaveness et al. |
| 5,827,531 | A | 10/1998 | Morrison et al. |
| 5,830,178 | A | 11/1998 | Jones et al. |
| 5,833,361 | A | 11/1998 | Funk |
| 5,846,518 | A | 12/1998 | Yan et al. |
| 5,855,615 | A | 1/1999 | Bley et al. |
| 5,863,957 | A | 1/1999 | Li et al. |
| 5,876,372 | A | 3/1999 | Grabenkort et al. |
| 5,877,224 | A | 3/1999 | Brocchini et al. |
| 5,885,216 | A | 3/1999 | Evans, III et al. |
| 5,885,547 | A | 3/1999 | Gray |
| 5,891,155 | A | 4/1999 | Irie |
| 5,895,411 | A | 4/1999 | Irie |
| 5,899,877 | A | 5/1999 | Leibitzki |
| 5,902,832 | A | 5/1999 | Van Bladel et al. |
| 5,922,025 | A | 7/1999 | Hubbard |
| 5,928,626 | A | 7/1999 | Klaveness et al. |
| 5,951,160 | A | 9/1999 | Ronk |
| 5,959,073 | A | 9/1999 | Schlameus et al. |
| 6,003,566 | A | 12/1999 | Thibault et al. |
| 6,015,546 | A | 1/2000 | Sutton et al. |
| 6,027,472 | A | 2/2000 | Kriesel et al. |
| 6,028,066 | A | 2/2000 | Unger |

(56) References Cited

U.S. PATENT DOCUMENTS

| | | | |
|---|---|---|---|
| 6,047,861 A | 4/2000 | Vidal et al. | |
| 6,051,247 A | 4/2000 | Hench et al. | |
| 6,059,766 A | 5/2000 | Greff | |
| 6,060,053 A | 5/2000 | Atala | |
| 6,063,068 A | 5/2000 | Fowles et al. | |
| 6,071,497 A | 6/2000 | Steiner et al. | |
| 6,073,759 A | 6/2000 | Lamborne et al. | |
| 6,090,925 A | 7/2000 | Woiszwillo et al. | |
| 6,096,344 A | 8/2000 | Liu et al. | |
| 6,099,864 A | 8/2000 | Morrison et al. | |
| 6,100,306 A | 8/2000 | Li et al. | |
| 6,139,963 A | 10/2000 | Fujii et al. | |
| 6,149,623 A | 11/2000 | Reynolds | |
| 6,162,377 A | 12/2000 | Ghosh et al. | |
| 6,165,193 A | 12/2000 | Greene, Jr. et al. | |
| 6,191,193 B1 | 2/2001 | Lee et al. | |
| 6,214,331 B1* | 4/2001 | Vanderhoff et al. | 424/78.17 |
| 6,224,630 B1 | 5/2001 | Bao et al. | |
| 6,224,794 B1 | 5/2001 | Amsden et al. | |
| 6,235,224 B1 | 5/2001 | Mathiowitz et al. | |
| 6,238,403 B1 | 5/2001 | Greene, Jr. et al. | |
| 6,258,338 B1 | 7/2001 | Gray | |
| 6,261,585 B1 | 7/2001 | Sefton et al. | |
| 6,264,861 B1 | 7/2001 | Tavernier et al. | |
| 6,267,154 B1 | 7/2001 | Felicelli et al. | |
| 6,268,053 B1 | 7/2001 | Woiszwillo et al. | |
| 6,268,405 B1* | 7/2001 | Yao | A61L 27/16 264/28 |
| 6,277,392 B1 | 8/2001 | Klein | |
| 6,291,605 B1 | 9/2001 | Freeman et al. | |
| 6,306,418 B1 | 10/2001 | Bley | |
| 6,315,709 B1 | 11/2001 | Garibaldi et al. | |
| 6,335,384 B1 | 1/2002 | Evans et al. | |
| 6,344,182 B1 | 2/2002 | Sutton et al. | |
| 6,355,275 B1 | 3/2002 | Klein | |
| 6,394,965 B1 | 5/2002 | Klein | |
| 6,419,624 B1 | 7/2002 | Burton et al. | |
| 6,423,332 B1 | 7/2002 | Huxel et al. | |
| 6,425,854 B1 | 7/2002 | Galt et al. | |
| 6,432,437 B1 | 8/2002 | Hubbard | |
| 6,478,775 B1 | 11/2002 | Galt et al. | |
| 6,537,574 B1 | 3/2003 | Hubbard | |
| 6,548,592 B1 | 4/2003 | Lang et al. | |
| 6,652,883 B2* | 11/2003 | Goupil et al. | 424/489 |
| 7,094,369 B2 | 8/2006 | Buiser et al. | |
| 7,131,997 B2* | 11/2006 | Bourne et al. | 623/23.72 |
| 7,185,657 B1* | 3/2007 | Johnson et al. | 128/898 |
| 7,611,542 B2* | 11/2009 | Bourne et al. | 623/23.72 |
| 8,394,400 B2* | 3/2013 | Bourne et al. | 424/423 |
| 8,586,071 B2* | 11/2013 | Bourne et al. | 424/423 |
| 2001/0016210 A1 | 8/2001 | Mathiowitz et al. | |
| 2001/0036451 A1 | 11/2001 | Goupil et al. | |
| 2001/0051670 A1 | 12/2001 | Goupil et al. | |
| 2002/0018752 A1 | 2/2002 | Krall et al. | |

FOREIGN PATENT DOCUMENTS

| | | |
|---|---|---|
| EP | 0 402 031 | 12/1990 |
| EP | 0 470 569 A1 | 2/1992 |
| EP | 0 547 530 B1 | 6/1993 |
| EP | 0 706 376 B1 | 4/1996 |
| EP | 0 730 847 A1 | 9/1996 |
| EP | 0 744 940 B1 | 12/1996 |
| EP | 0 797 988 A2 | 10/1997 |
| EP | 0 826 381 A2 | 3/1998 |
| EP | 0 623 012 B1 | 11/2004 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-316271 | 12/1997 |
| JP | 10-130329 | 5/1998 |
| WO | WO/92/21327 A1 | 12/1992 |
| WO | WO/93/19702 A1 | 10/1993 |
| WO | WO/94/10936 A1 | 5/1994 |
| WO | WO/95/03036 A1 | 2/1995 |
| WO | WO/95/22318 A1 | 8/1995 |
| WO | WO/96/37165 A1 | 11/1996 |
| WO | WO/96/39464 A1 | 12/1996 |
| WO | WO/98/04616 A1 | 2/1998 |
| WO | WO/98/10798 A1 | 3/1998 |
| WO | WO/99/12577 A1 | 3/1999 |
| WO | WO/99/57176 A1 | 11/1999 |
| WO | WO/00/23054 A1 | 4/2000 |
| WO | WO/00/40259 A1 | 7/2000 |
| WO | WO/00/71196 A1 | 11/2000 |
| WO | WO/00/74633 A2 | 12/2000 |
| WO | WO/01/70291 A2 | 9/2001 |
| WO | WO/02/11696 A2 | 2/2002 |
| WO | WO/02/34298 A1 | 5/2002 |
| WO | WO/02/34299 A1 | 5/2002 |
| WO | WO/02/34300 A1 | 5/2002 |
| WO | WO/02/43580 A2 | 6/2002 |
| WO | 03082359 | 10/2003 |

OTHER PUBLICATIONS

The Cleveland Clinic website, "Urology News," *Two New Techniques for Incontinence*, http://www.clevelandclinic.org/urology/news/incontinence/vol7j.htm, 2 pages, (downloaded Jun. 5, 2002).

Bachtsi, A.R. et al., "An experimental investigation of Enzyme Release from Poly (vinyl alcohol) crosslinked Microspheres", J. Microencapsulation, vol. 12, No. 1, pp. 23-35; 1995.

Barr, J.D., et al., "polyvinyl Alcohol Foam Particles Sizes and Concentrations Injectable through Microcatheters", JVIR, vol. 9, No. 1, pp. 113-118; 1998.

Barttinelli, L. et al., "New Class of Poly (vinyl alcohol) Polymers as Column-Chromatography Stationary Phases for Candida Rugosa Lipase Isoforms Separation", J. Chromatogr A, vol. 753, No. 1, pp. 47-55; 1996. Abstract. http://www.ncbi.nlm.nih.gov/entrez/query.fcgi?.

Berenstein, A. et al., "Catherer and Material Selection for Transarterial Embolization: Technical Considerations. I. Materials", Radiology, vol. 132, No. 3, pp. 631-639; 1979.

Berenstein, A. et al., "Microembolization Techniques of Vascular Occlusion: Radiologic, Pathologic, and Clinical Correlation", AJNR Am I Neuroradiol, vol. 2, No. 3, pp. 261-267; 1981. Abstract, http://www.ncbi.nlm.nih.gov/entrez/query.fcgi?.

Bruix,J. et al., "Transarterial Embolization Versus Symptomatic Treatment in Patients With Advanced Hepatocellular Carcinoma; Results of a Randomized, Controlled Trial in a Single Institution", Hepatology, Jun. 1998, vol. 27, No. 6, pp. 1578-1583. Available Web Site: http://www.hepatitis-central.com/hcv/hcc/embolization/references.html.

Buhle, Jr., EL, "Re: Hepatic Arterial Embolization", UCLA Medicine Online, Available Web Site: http://www.meds.com/archive/mol-cancer/1996/msg00128.html Downloaded Jan. 6, 2007.

Burczak, et al., "Long-term in vivo performance and biocompatinility of poly (vinyl alcohol) hydrogel macrocapsules for hybrid-type artificial pancreas", Biomaterials, vol. 17, No. 24, pp. 2351-2356, 1996, abs: http://www.ncbi.nlm.nih.gov/entrez/query.fcqi?cmd=retrieve&db=pubmed&list_uids=89824 . . . , pp. 1, 02.

Burczak, et al., "Polymaric materials for biomedical purposes obtained by radiation methods. V. hybrid artificial pancreas", Polim Med, vol. 24, No. 1-2, pp. 45-55, 1994, abs: http://www.ncbi.nlm.nih.gov/entrez/query.fcgi?cmd=retrieve&db=PubMed&list_uids=7915 . . . , pp. 1, 02.

Choe, et al., "An experimental study of embolic effect according to infusion rate and concentration of suspension in transarterial particulate embolization", Invest Radiol, vol. 32, No. 5, pp. 260-270, 1997, Abs: http://www.ncbi.nlm.nih.gov/entrez/query.fcgi?cmd=retrieve&db=PubMed&list_uids=9140745&dopt+Abs . . . , pp. 1, 02.

Chuang, et al., "Experimental Canine Hepatic Artery Embolization with Polyvinyl Alcohol Foam Particles", Departments of Diagnostic

(56) References Cited

OTHER PUBLICATIONS

Radiology and Veterinary Medicine, the University of Texas, M.D. Anderson Hospital and Tumor Institute at Houston, Texas, pp. 21-25. 1982.

Clarian Health Methodist—Indiana Lions Gamma Knife Center, "Arteriovenous Malformation" Available Web Site: http://www.clarian.com/tyhealth/gammaknife/cond_arter.asp Mar. 5, 2003.

Colombo M, "Treatment of Hepatocellular Carcinoma", University of Milan, Inst Internal Med, Irccs Maggiore Res Unit Liver, Canc, Firc, via Pace 9 1-20122 Milan, Italy. Source: Journal of Viral Hepatitis, 1997; 4:125-130. Available Web Site: http://www.home.texoma.net/~moreland/stats/hcc-9.html.

Derdeyn, et al., "Collagen-coated acrylic microspheres for embolotherapy: in vivo and in vitro characteristic", American Journal of Neuroradiology, vol. 18, No. 4, pp. 647-653, 1997 abs: http://www.ncbi.nlm.nih.gov/entrez/query.fcgi?cmd=retrieve&db=PubMed&list_uids=9127025&dopt=Abs . . . , pp. 1, 02.

Derdeyn, et al., "Polyvinyl alcohol particle size and suspension characteristics", American Journal of Neuroradiology, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, Jan. 1994, vol. 83, No. 1, pp. 104-106.

Gander, et al., "Effect of polymeric network structure on drug release from cross-linked poly (vinyl alcohol) micromatrices", Pharm Res., vol. 6, No. 7, pp. 578-584, 1989, abs: http://www.ncbi.nlm.nih.gov/entrez/query.fcgi?cmd=retrieve&db=PubMed&list_uids=25080 . . . , pp. 1, 02.

Germano, et al., "Histopathological follow-up study of 66 cerebral arteriovenous malformations after therapeutic embolization with polyvinyl alcohol", J Neurosurg, vol. 76, No. 4, pp. 607-614, 1992, abs: http://www.ncbi.nlm.nih.gov/entrez/query.fcgi?cmd=retrieve&db=PubMed&list_uids=15452 . . . , pp. 1, 02.

Geschwind et al., "Chemoembolization of Liver Tumor in a Rabbit Model: Assessment of Tumor Cell Death with Diffusion-Weightened MR Imaging and Histologic Analysis", Journal of Vascular and Interventional Radiology, Dec. 2000, vol. 11., No. 10, pp. 1245-1255.

Gohel, et al., "Formulation designed and optimization of modified-release microspheres of diclofenac sodium", Drug Dev Ind Pharm, vol. 25, No. 2, pp. 247-251, 1999, abs: http://www.ncbi.nlm.nih.gov/entrez/query.fcgi?cmd=retrieve&db=PubMed&list_uids=100653605&dop=A . . . , pp. 1, 02.

Goodwin, et al., "Overview of embolic agents and their indications", Eleventh Annual International Symposium on Endovascular Therapy, pp. 303-306, 1999.

Goodwin, et al., "Preliminary experience with uterine artery embolization for uterine fibroids", Journal of Vascular and Interventional Radiology, vol. 8, No. 4, pp. 517-526, 1997.

Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992, abs: http://www.ncbi.nlm.nih.gov/entrez/query.

Hamada, et al., "Embolization withcellulose porous beads, II: Clinical Trial," abs: http://www.ojnr.org/content/abstract/17/10/1901?ijkey=R.a2vRMietlXw, pp. 1-2, 02. 1996.

Horak, et al., "Hydrogels in endovascular embolization. II. Clinical use of spherical particles", Biomaterials, vol. 7, 1986.

Huang, et al., "Percutaneous endovascular embolization of intracerebral arteriovenous malformations. Experience in 72 cases", Chin Med J, vol. 108, No. 6, pp. 413-419, 1995 abs: http://www.ncbi.nlm.nih.gov/entrez/query.fcgi?cmd=retrieve&db=PubMed&list_uids=75552s . . . , pp. 1, 02.

International Search Report for International Application No. PCT/Us01/06981 (2 pages).

Jack, et al., "Radiolabeled polyvinyl alcohol particles: a potential agent to monitor embolization procedures", Int J Rad Appl Instrum B, vol. 13, No. 3, pp. 235-243, 1986, abs: http://www.ncbi.nlm.nih.gov/entrez/query.fcgi?cmd=retrieve&db=PubMed&list_uids=37712, pp. 1, 02.

Joy C, et al., 1991, "Use of Preoperative Embolization in the Treatment of Vascular Metastatic Lesions of the Spine" Available Web Site: http://www.aaos.org/wordhtm/anmeet91/scipro/ppr472.htm.

Kai, et al., "The utility of the microcrystalline cellulose sphere as a particulate embolic agent: an experimental study", American Journal of Radiology, vol. 21, No. 6, pp. 1160-1163, 00, or http://www.ajnr.org/cgi/content/full/21/6/1160, 2000, pp. 1-7.

Kan, et al., "In vivo microscopy of the liver after injection of lipiodol into the hepatic artery and portal vein in the rat", Acta Radiologica, vol. 30, pp. 419-425, 1989.

Kerber, et al., "Polyvinyl Alcohol Foam: Prepackaged Emboli for Therapeutic Embolization", American Journal Roentgenol, Jun. 1978, vol. 130, pp. 1193-1194.

Kerber, "Flow-Controlled Therapeutic Embolization: A Physiologic and Safe Technique", AJR, Mar. 1980, vol. 134, pp. 557-561.

Kim, et al., "Composite poly(vinyl alcohol) beads for controlled drug delivery", Pharm Res, vol. 9, No. 1, pp. 10-16, 1992 abs: http://www.ncbi.nlm.nih.gov/entrez/query.fcgi?cmd=retrieve&db=PibMed&list_uids=1589392&dpot=Abs . . . , pp. 1, 02.

Kurata, et al., "Preoperative embolization for meningiomas using PVA particles", No Shinkei Geka, vol. 20, No. 4, pp. 367-373, 1992, abs: http://www.ncbi.nlm.nih.gov/entrez/query.fcgi?cmd=retrieve&db=PubMed&list_uids=1570057&dopt=Abs . . . , pp. 1, 02.

Kurosaki, et al., "Evaluation of PVA-Gel Spheres as GI-Transit Time Controlling Oral Drug Delivery System", Proceedings of the 19$^{th}$ International Symposium on Controlled Release of Bioactive Materials, Jul. 26-31, 1992, Orlando, Florida, pp. 273-274.

Kusano, et al., "Low-dose particulate polyvinylalcohol embolization in massive small artery intestinal hemorrhage. Experimental and clinical results", Invest Radiol, vol. 22, No. 5, pp. 338-392, 1987, abs: http://www.ncbi.nlm.gov/entrez/query.fcgi?cmd=retrieve&db=PubMed&list_uids=34963 . . . , pp. 1, 02.

Labarre, et al., Complement activation by substituted polyacrulamide hydrogels for embolization and implantation, Biomaterials, vol. 23, pp. 2319-2327, 2002.

Lammer, et al., "Transcatheteral embolization with polyvinyl alcohol-technic and experimental studies," Rontgenblatter, vol. 36, No. 1, pp. 10-14, 1983, abs: http://www.ncbi.nlm.nih.gov/entrez/query.fcgi?cmd=retrieve&db=PubMed&list_uids=6823530&dopt=Abs . . . , pp. 1, 02.

Latchaw, et al., "Polyvinyl Foam Embolization of Vascular and Neoplastic Lesions of the Head, Neck, and Spine", Radiology, Jun. 1979, vol. 131, pp. 669-679.

Leung, et al., "Determinants of Postembolization Syndrome after Hepatic Chemoembolization", Journal of Vascular and Interventional Radiology, Mar. 2001, vol. 12, No. 3, pp. 320-326.

Markoff, et al., "Uterine arteriovenous malformation successfully embolized with a liquid polymer, isobutyl 2-cyanoacrylate", pp. 659-660, 1999.

Matsumaru, et al., "Embolic materials for endovascular treatment of cerebral lesions," J Biometer Sci Polym Ed, vol. 8, No. 7, pp. 555-569, 1997, abs: http://www.ncbi.nlm.nih.gov/entrez/query.fcgi?cmd=retrieve&db=PubMed&list_uids=91953& . . . , pp. 1, 02.

Mid-America Interventional Radiological Society, New Treatment for Uterine Fibroids Avoids Surgery: Available Web Site: http://www.mirs.org/fibroids.htm 2003.

Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997, abs: http://www.ncbi.nlm.nih.gov/entrez/query.fcgi?cmd=retrieve&db=PubMed&list_uids=90904 . . . , pp. 1-2, 02.

Nakstad, et al., "Embolization of intracranial arteriovenous malformations and fistulas with polyvinyl alcohol particles and platinum fibre coils", Neuroradiology, vol. 34, No. 4, pp. 348-351, 1992, abs: http://www.ncbi.nlm.nih.gov/entrez/query.fcgi?cmd=retrieve&db=PubMed&list_uids=15284 . . . , pp. 1, 02.

Nash, et al., "Modifications of polystyrenic matrices for the purification of proteins. II. Effect of the degree of glutaraldehyde-

(56) References Cited

OTHER PUBLICATIONS poly(vinyl alcohol) crosslinking on various dye ligand chromatography systems", J. Chromatogr A, vol. 776, No. 1, pp. 55-63, 1997, abs: http://www.ncbi.nlm.nih.gov/entrez/query.fcgi?cmd=retrieve&db=PubMed&list_uids=92860 . . . , pp. 1, 02.

Nikishin LF, et al., 1999, "Interventional radiology in diffuse toxic goiter", European Congress of Radiology-ECR 1999, Available Web Site: http://www.ecr.org/conference/ecr1999/sciprg/abs/p090041.htm.

Ophir, et al., "Ultrasonic backscatter from contrast producing collagen microspheres", Ultrasonic Imaging, vol. 2, pp. 67-77, 1980.

Oregon Health Sciences University, "Fibroid Embolization", Available Web Site: http://www.uhmc.edu/dotter-fibroid. Jun. 2001.

Parker, et al., "A particulate contrast agent with potential for ultrasound imaging of liver", Ultrasounds in Medicine and Biology, vol. 13, No. 9, pp. 555-566, 1987.

Pesant A.C., et al., 1997, "Dural fistulas involving the cavernous sinus: Treatment by embolization—7 cases", European Congress of Radiology—ECR 1997, Available Web Site: http://www.ecr.org/conferences/ecr1997/sciprg/abs/9703008p.htm.

Physicans' Desk Reference Family Guide to Women's Health, "Chapter 1—Guide to Typical Sympton and Their Meaning", Available Web Site: http://www.healthsquare.com/pdrfg/wh/chapters/wh1ch01.htm , Pub. Jan. 15, 1994.

Pritchard, et al., "Poly(vinyl Alcohol): Basic Properties and Uses", London, England: Gordon and Breach Science Publishers. 1970.

Pryor J and Berenstein A., Epistaxis(Nose-bleeds), Available Web Site: http://www.wehealny.com/inn/Radiology/nosebleeds.html, Mar. 9, 2001.

Purdy, et al., "Arteriovenous malformations of the brain: choosing embolic materials to enhance safety and ease of excision", J Neurosurg., vol. 77, No. 2, pp. 217-222, 1992, abs: http://www.ncbi.nlm.nih.gov/entrez/query.fcgi?cmd=retrieve&db=PubMed&list_uids=16250 . . . , pp. 1-2, 02.

Quisling, et al., "Histopathology analysis of intraarterial polyvinyl alcohol microemboli in rat cerebral cortex", American Journal of Neuroradiology, vol. 5, pp. 101-104, 1984.

Rajan, et al., "Sarcomas Metastatic to the liver: Response and Sirvival after Cisplatin, Doxorubicin, Mitomycin-C, Ethiodol, and Polyvinyl Alcohol Chemoembolization", Journal of Vascular and Interventional Radiology, Feb. 2001, vol. 12, No. 2, pp. 187-193.

Ramos, et al., "Tumor vascular signals in renal masses: detection with Doppler US", Radiology, vol. 168, No. 3, pp. 633-637, 1988.

Shakif, A., "Intraesophageal Polytef injection for the treatment of reflux esophagitis", *Department of Surgery and Experimental Research*, Faculty of Medicine, Cairo University, Cairo, Egypt, pp. 1-2, Accepted: Oct. 15, 1994, http://www.ahmedshakif.org/Group-D/d016.htm.

Spickler, et al., "The MR appearance of endovascular embolic agents in vitro with clinical correlation", Comput Med Imaging Graph, vol. 14, No. 6, pp. 415-423, 1990, abs: http://www.ncbi.nlm.nih.gov/entrez/query.fcgi?cmd=retrieve&db=PubMed&list_uids=21487 . . . , pp. 1, 02.

Spies JB, "Georgetown University Medical Center. Uterine Fibroid Embolization (UFE). An alternative to surgery for patients with uterine fibroids. Literature Review." Available Web Site: http://www.dml.georgetown.edu/fibroids, Sep. 1, 2001.

Strunk, et al., "Treatment of congenital coronary arteriovenous malformations with microparticle embolization", Cathet Cardiovasc Diagn., vol. 22, No. 2, pp. 133-136, 1991, abs: http://www.ncbi.nim.nih.gov/entrez/query.fcgi?cmd=retrieve&db=PubMed&list_uids=2009563&dopt=Abs . . . , pp. 1, 02.

Swanson DA et al., 1980, "The role of embolization and nephrectomy in the treatment of metastatic renal carcinoma", Urologic Clinics of North America 7(3):719-730, 1980. University of Pennsylvania Cancer Center-Oncolink. Available Web Site: http://www.oncolink.upenn.edu/pdg.html/cites/00/00585.html.

Tabata, et al., "Tumor accumulation of poly(vinyl alcohol) of different sizes after intravenous injection", Journal of Controlled Release, Jan. 2, 1998, vol. 50, Nos. 1-3, pp. 123-133.

Tadavarthy, et al., "Polyvinyl Alcohol (Ivalon) as an Embolizing Agent", The American Journal of Roentgenology Radium Therapy and Nuclear Medicine, Nov. 1975, vol. 125, No. 3, pp. 609-616.

Tadavarthy, et al., "Polyvinyl Alcohol (Ivalon) as an Embolizing Agent", Seminars in Interventional Radiology, vol. 1, No. 2, Department of Radiology, University of Minnesota Hospitals, Minneapolis, Minnesota, Jun. 1984, pp. 101-109. 2001.

Tao, et al., "Study on embolization of hepatitis artery using microspheres", Acta Pharmaceutica Sinica, vol. 23, No. 1, pp. 55-60; 1988. Translation.

Terada, et al., "Preoperative embolization of meningiomas fed by ophthalmic branch arteries", Surg Neurol, vol. 45, No. 2, pp. 161-166, 1996, abs: http://www.ncbi.nlm.nih.gov/entrez/query.fcgi?cmd=retrieve&db=PubMed&list_uids=86070 . . . , pp. 1, 02.

Thanoo, et al., "Controlled release of oral drugs from cross-linked polyvinyl alcohol miscrospheres", J Pharm Pharmacol, vol. 45, No. 1, pp. 16-20, 1993, abs: http://www.ncbi.nlm.nih.gov/entrez/query.fcgi?cmd=retrieve&db=PubMed&list_uids=8094434&dop=Abs . . . , pp. 1, 02.

Thanoo, et al., "Tantalum loaded silicone microspheres as particulate emboli", J. Microencapsul, vol. 8, No. 1, pp. 95-101, 1991, abs: http://www.ncbi.nlm.nih.gov/entrez/query.fcgi?cmd=retrieve&db=PubMed&list_uids=1880697&dop=Abs . . . , pp. 1, 02.

The Fibroid Embolization Center of the New York United Hospital Medical Center, "Fibroid Facts", Available Web Site: http://www.uhmc.com/fibro2.htm, Apr. 29, 1999.

The Vanderbilt-Ingram Cancer Center, "Kidney Cancer." Available Web Site: http://www.mc.Vanderbilt.Edu/cancer/cancerinfo/kidney.html, Sep. 18, 2000.

Tikkakoski, et al., "Preoperative embolization in the management of neck paragangliomas", Laryngoscope, vol. 107, pp. 821-826, 1997.

Touho, et al., "Intravascular treatment of spinal arteriovenous malformation using a microcatheter with special reference to serial xylocaine tests and intravascular pressure monitoring", Surgical Neurology, vol. 42, No. 2, pp. 148-156, 1994, abs: http://www.ncbi.nlm.nih.gov/entrez/query.fcgi?cmd=retrieve&db=PubMed&list_uids=80912 . . . , pp. 1, 02.

UCLA Radiological Sciences, "A summary of terms appearing in this text." Available Web Site: http://www.radsci.ucla.edu:8000/aneurysm/terms.html,Aug. 19, 2000.

University Medical Center SUNY Stony Brook, Department of Urology, "Variocele and its treatment." Available Web Site: http://www.hsc.sunysb.edu/urology/male_inf...variocele_and_its)treatment.html, Mar. 12, 2001.

Vivas S., et al., "Arterioportal fistula and hemobilia in a patient with hepatic transplant", Gastroenterol Hepatol, Feb. 1998;21(2):88-9, Available Web Site: http://www.doyma.es/copiani/revistas/gastro/abstr/abs_p080.html.

Vogel F., "Nonsurgical Management of Uterine Fibroids", Available Web Site: http://www.holyname.org/brochure/fibroids.html, Mar. 4, 1998.

Wakhloo, et al., "Extended preoperative polyvinyl alcohol microembolization of intracranial meningiomas: Assessment of two embolization techniques", American Journal of Neuroradiology, vol. 14, pp. 571-582, 1993.

Walker WJ, "Non Surgical Treatment of Fibroids in the UK by Uterine Artery Embolisation—An Alternative to Hysterectomy, Myomectomy, and Myolysis", Available Web Site: http://www.fibroids.co.uk/thepaper.html, Oct. 19, 1999.

Wikholm G, et al., 1996, "Embolization of Cerebral Arteriovenous Malformations: Part 1—Technique, Morphology, and Complications", Departments of Neurology (CL) and Interventional Radiology (GW, PS) Sahlgrenska University Hospital, Goteborg, Sweden. Neurosurgery. Sep. 1996;39(3):448-57;discussion 457-9. Available Web Site: http://www.wwilkins.com/neurosurgery/0148-396X9-96inter.html.

Worthington-Kirsch RL, 1999, "Interventionalists offer management option for uterine fibroids." Diagnostic Imaging, pp. 47-49. Available Web Site: http://www.dimag.com/references/9903wortrefs.html.

Worthington-Kirsch, et al., "Uterine arterial embolization for the management of leiomyomas: Quality-of-life assessment and clinical response", Radiology, vol. 208, No. 3, 625-629, 1998.

(56) References Cited

OTHER PUBLICATIONS

Yamada, et al., "Extended intraarterial cisplatin infusion for treatment of gynecological cancer after alteration of intrapelvic blood flow and implantation of a vascular access device", International Radiology, Int'l Radiology 19 1996 139-145.

* cited by examiner

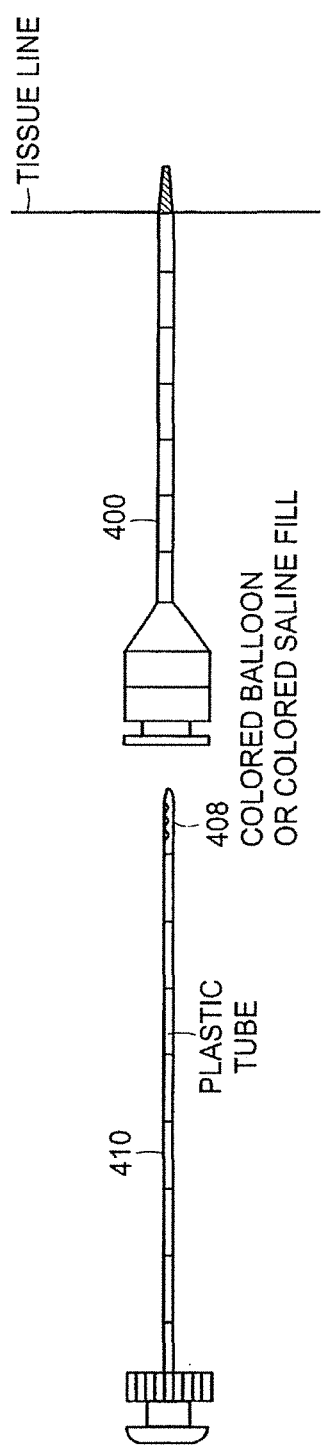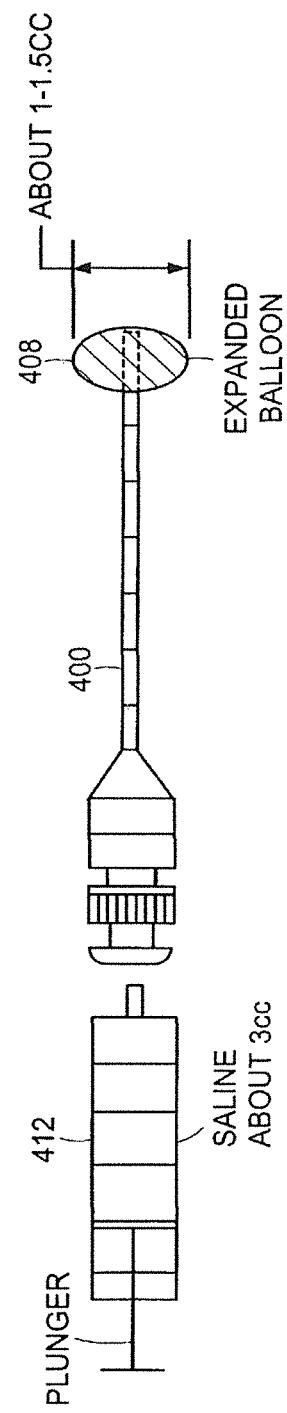
FIG. 6
FIG. 7

BULKING AGENTS

CROSS-REFERENCE TO RELATED APPLICATION

This application is a divisional of co-pending U.S. patent application Ser. No. 13/792,346, filed Mar. 11, 2013, which is a divisional of U.S. patent application Ser. No. 12/946,990, filed on Nov. 16, 2010, now U.S. Pat. No. 8,394,400 which is a divisional of Ser. No. 10/459,895, filed Jun. 12, 2003, which claims the benefit of provisional U.S. patent application Ser. No. 60/388,446, which was filed on Jun. 12, 2002, all of which are incorporated by reference in their entireties herein.

TECHNICAL FIELD

The invention relates generally to the treatment of mammalian tissue through the process of bulking, and more specifically to the injection of bulking particles into a treatment region of a mammal

BACKGROUND

Urinary incontinence, vesicourethral reflux, fecal incontinence, and intrinsic sphincter deficiency (ISD), for example, are disorders that have responded to treatments with augmentative materials. Such disorders occur when the resistance to flow of bodily discharges decreases to the point where the resistance can no longer overcome the intra-abdominal pressure. Nearly all procedures developed to restore continence are based on restoring the lost resistance.

Surgical implantation of artificial sphincters has often been employed to treat patients suffering from urinary incontinence. The surgical implantation of the artificial sphincter commonly requires hospitalization, is relatively complex and expensive, and will usually require six to eight weeks of recovery time. Moreover, the procedure may be unsuccessful if the artificial sphincter malfunctions. As a result, additional surgery is required to adjust, repair, or replace the implant.

Urinary incontinence can also be treated using nonsurgical means. A common method to treat patients with urinary incontinence is periurethral injection of a bulking materiaL One such bulking composition is a Teflon® paste known commercially as "Polytef" or "Urethrin." This paste is comprised of a fifty-fifty (50-50) by weight mixture of a glycerin liquid with Teflon® (polytetrafluoroethylene (PTFE)) brand particles sold by DuPont. The glycerin is biodegradable, however, and over a period of time the glycerin dissipates into the body and is then metabolized or eliminated leaving only about fifty percent (50%) of the injected mixture (i.e., the Teflon® particles) at the injection site. Consequently, to achieve the desired result, the surgeon typically overcompensate for the anticipated loss of bulking material by injecting a significantly larger amount of material than initially required. At the extreme, this overcompensation can lead to complete closure of the urethra, which could put the patient into temporary urinary retention. Additionally, the eventual dissipation of the glycerin complicates the surgeon's ability to visually gauge the appropriate amount of bulking material to inject. To avoid these over-bulking side effects, the surgeon may ultimately not inject enough bulking mixture, leading to the likelihood of a second or even a third procedure to inject additional material.

Further, the particle size in the Teflon® paste bulking material if sufficiently small may allow the particles to migrate to other locations of the body, such as the lungs, brain, etc. Teflon® particles have been known to induce undesirable tissue reaction and form Teflon® induced granulomas in certain individuals.

In addition, the Teflon® paste is typically highly viscous and can only be injected using a hypodermic needle held by an injection assist device. Use of an injection assist device may be required, because a surgeon would likely not have sufficient strength to force the highly viscous Teflon® paste through a needle of any acceptable size.

Two alternatives to the Teflon® paste are a collagen gel and carbon coated zirconium beads. One such commercially available product includes Contigen®, available from CR Bard. The collagen gel is injected in the same manner as the Teflon® paste and forms a fibrous mass of tissue around the augmentation site. This fibrous mass created by the collagen injection, however, also dissipates over time and is eventually eliminated by the patient's body. As a result, additional injections are periodically required.

Yet another bulking procedure includes the injection of swollen hydrogel particles. The swollen hydrogel particles exhibit relatively low injection forces by incorporating low molecular weight water-soluble organic compounds, along with water, in the particles. See, for example, U.S. Pat. Nos. 5,813,411 and 5,902,832 to Van Bladel et al., and U.S. Pat. No. 5,855,615 to Bley et al., the disclosures of which are hereby incorporated herein by reference in their entireties.

Another alternative to the Teflon paste is a hard particle suspension. One such commercially available product is Durasphere® available from Carbon Medical Technologies. These hard particles, for example carbon coated zirconium beads, are injected in a beta-glucan carrier. The beta-glucan is eliminated by the patient's body over time. As a result, additional injections may be required. Furthermore, hard particle suspensions, depending on the size of the particle, may tend not to be easily dispensed without clogging smaller gauge injection needles.

Furthermore, available methods of injecting bulking agents require the placement of a needle at a treatment region, for example, peri-urethrally or transperenially. Assisted by visual aids, the bulking agent is injected into a plurality of locations, causing the urethral lining to coapt. In cases where additional applications of bulking agent are required (e.g., when bulking agents are dissipated within the body), the newly added bulking agent may need to be injected at a higher pressure than the pressure at which the initial bulking agent was injected. The higher pressure requirements for subsequent injections may result from the effect of closing off the treatment region by the initial bulking agent, thereby creating backpressure when attempting to insert additional bulking agent(s). Typically, the bulking agent is injected at multiple locations to cause the uretheal lining to coapt with a higher opening pressure than the patient had prior to injection of the bulking agent.

Bulking agent delivery methods have attempted to address the issue of subsequent injection requirements. One method that has been employed is hydrodissection of tissue in the vicinity of the treatment region, thereby creating tissue voids designed to decrease the injection pressure required when adding additional bulking agent to the voids. Another method used to reduce injection pressures is the Urovive™ device available from American Medical Systems. Urovive™ utilizes a plurality of silicone balloons that are inserted into the treatment region, specifically, the periphery of the sphincter. The balloons are then filled with a hydrogel to effect tissue coaptation.

SUMMARY OF THE INVENTION

The invention generally relates to an injectable bulking composition that does not degrade or dissipate in the body, has sufficiently low viscosity such that it is easily administered via injection, and will not migrate from the site of injection, thereby enabling the affected tissue to maintain the desired constriction without causing undesirable side effects. In addition, the invention generally relates to an injection method that reduces the injection pressure required to place the bulking agents.

In one aspect the invention relates to the use of polymeric particles to facilitate bulking in a treatment region of a mammal's body through injection of the particles into the treatment region. The particles are compliant enough to be delivered through a relatively small gauge injection device. Generally, the invention is employed in the treatment of diseases requiring sphincter bulking, e.g., for treating urinary or fecal incontinence; however, the bulking method described herein can also be used for soft tissue bulking for use during, for example, plastic surgery.

In another aspect the invention relates to a bulking agent for medical applications. The bulking agent includes a carrier and a plurality of substantially spherical polyvinyl alcohol particles dispersed within the carrier. The carrier aids the delivery of the substantially spherical polyvinyl alcohol particles to a site to be bulked.

In yet another aspect, the invention relates to a method for bulking mammalian tissue. The method includes the steps of introducing a bulking agent to the mammalian tissue to coapt the mammalian tissue with the bulking agent. The bulking agent includes a carrier and a plurality of substantially spherical polyvinyl alcohol particles dispersed within the carrier. The carrier aids the delivery of the substantially spherical polyvinyl alcohol particles to a site to be bulked.

In various embodiments of the foregoing aspects, the bulking agent comprises a volume. The volume could be, for example, from about 1 ml to about 30 ml, from about 20 ml to about 30 ml, or from about 2 ml to about 16 ml. In additional embodiments, the substantially spherical polyvinyl alcohol particles are sized from about 40 micron to about 1500 microns in diameter, preferably from about 150 micron to about 1100 microns in diameter, and more preferably from about 500 micron to about 900 microns in diameter. Further, the substantially spherical polyvinyl alcohol particles can comprise pores and/or bioreactive agents, such as drugs, proteins, genes, chemo-therapeutic agents, and growth factors. In other embodiments, the substantially spherical polyvinyl alcohol particles can be compressible and/or substantially dimensionally stable.

In additional embodiments, the carrier can be a water-based solution, such as saline solution. In addition, the carrier can include at least one of a lubricant, a biocompatible thickening agent, or a color. Furthermore, the bulking agent can be delivered through a needle and/or a catheter. In one embodiment, the bulking agent is delivered transuretherally. In addition, the bulking agent can be delivered while viewing the tissue to be bulked with a cytoscope.

In still another aspect, the invention relates to an apparatus for bulking mammalian tissue. The apparatus includes a needle defining a lumen, an inflation device adapted to advance through the lumen of the needle, and a bulking agent insertable via the lumen of the needle. The needle is adapted to penetrate the mammalian tissue. The inflation device is disposed adjacent to the mammalian tissue after being advanced through the needle. The inflation device is inflatable and subsequently deflatable to create a void in the mammalian tissue. The bulking agent is inserted to fill at least partially the void in the tissue, the bulking agent coapting the mammalian tissue.

In various embodiments of the foregoing aspect of the invention, the inflation device can include a biocompatible balloon, and/or a color coating for visualization made from at least one of a silicone, an ethylene vinyl alcohol, a polypropylene, a latex rubber, a polyurethane, a polyester, a nylon, or a thermoplastic rubber. Additionally, the inflation device can have a shape selected from the group consisting of substantially round, oval, hemi spherical, spherical, or oblong. In one embodiment, the needle is sized from 16 gauge to 24 gauge, preferably from 18 gauge to 22 gauge.

In additional embodiments, the bulking agent comprises a plurality of polymeric particles and can be injected into the void by a syringe. In one embodiment, the bulking agent includes a carrier and a plurality of substantially spherical polyvinyl alcohol particles dispersed within the carrier. The carrier aids the delivery of the substantially spherical polyvinyl alcohol particles to a site to be bulked. The bulking agent can further include a color.

In yet another aspect, the invention relates to a method for bulking mammalian tissue. The method includes the steps of inserting an inflation device within a portion of a mammal, inflating the inflation device to compress the mammalian tissue surrounding the inflated inflation device, thereby creating a void in the tissue, deflating the inflation device, removing the inflation device from the mammal, and providing a bulking agent to at least partially fill the void, the bulking agent coapting the mammalian tissue.

In various embodiments of this aspect of the invention, the method includes the steps of inserting a needle with a penetration device into the mammalian tissue, removing the penetration device while retaining the inserted needle, and advancing the inflation device through the needle. The needle can be sized from 16 gauge to 24 gauge, preferably 18 gauge to 22 gauge. The method can also include the step of viewing the tissue to be bulked with a cytoscope. In one embodiment, the inflation device can include a biocompatible balloon, and/or a color coating for visualization made from at least one of a silicone, an ethylene vinyl alcohol, a polypropylene, a latex rubber, a polyurethane, a polyester, a nylon and a thermoplastic rubber. Additionally, the inflation device can have a shape selected from the group consisting of substantially round, oval, hemi spherical, spherical, or oblong.

In additional embodiments, the bulking agent comprises a plurality of polymeric particles and can be injected into the void by a syringe. In another embodiment, the substantially spherical polyvinyl alcohol particles are coated, embedded, or filled with a material that will aid the delivery of the particles to a site to be bulked. In one embodiment, the bulking agent includes a carrier and a plurality of substantially spherical polyvinyl alcohol particles dispersed within the carrier. The carrier aids the delivery of the substantially spherical polyvinyl alcohol particles to a site to be bulked. The bulking agent can further include a color.

These and other objects, along, with advantages and features of the present invention, will become apparent through reference to the following description, the accompanying drawings, and the claims. Furthermore, it is to he understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention. In the following description, various embodiments of the present invention are described with reference to the following drawings, in which:

FIG. 6 is a schematic plan view of the needle assembly of FIG. 4 with a balloon assembly being inserted into the needle assembly;

FIG. 7 is a schematic plan view of the needle assembly of FIG. 4 with a syringe attached to the needle assembly for inflating the balloon;

DESCRIPTION

Embodiments of the present invention are described below. The invention is not limited, however, to these embodiments. For example, various embodiments of the invention are described in terms of treating incontinence; however, embodiments of the invention may be used in other applications, such as cosmetic reconstruction.

Figure 1:
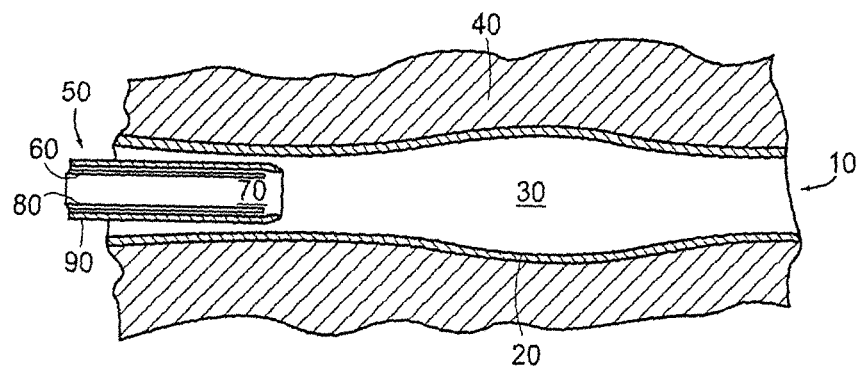
FIG. 1 depicts a side view of a tissue structure with an enlarged lumen surrounded by muscle tissue.

Referring to FIG. 1, a tissue structure, more specifically a urethra/ureter 10, having a wall 20 and an enlarged lumen 30 surrounded by muscle tissue 40 is shown in side view. Before the enlarged lumen 30 is constricted with the bulking composition, a cystoscope 50 comprising a fiberoptic light transmitting element 60, a working channel 70 and a viewing element 80 encased in a sheath 90 may be inserted in the urethra/ureter 10 to a distance close to the enlarged lumen 30. The close distance is selected to allow a clear view of the enlarged lumen 30.

Figure 2:
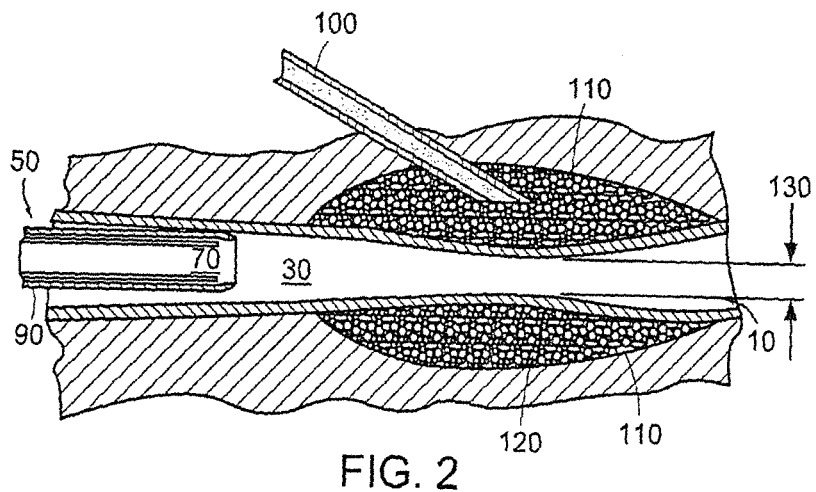
FIG. 2 depicts the tissue structure of FIG. 1 immediately ager a bulking agent in accordance with the invention has been injected around the enlarged lumen of the tissue.

Referring to FIG. 2, the urethra/ureter 10 is shown immediately after a bulking agent in accordance with the invention has been injected around the enlarged lumen 30 of the tissue. Once the enlarged lumen 30 is readily in view, a hypodermic needle 100 is inserted through the tissue 40, preferably over the enlarged lumen 30, stopping near the wall 20 of the enlarged lumen 30. Thereafter, a bulking agent 110 including polymeric particles 120 is injected via the hypodermic needle 100 into the tissue 40 adjacent the wall 20. The result is a constricted region 130 located in the vicinity of the accumulation of the bulking agent 110.

Figure 3:
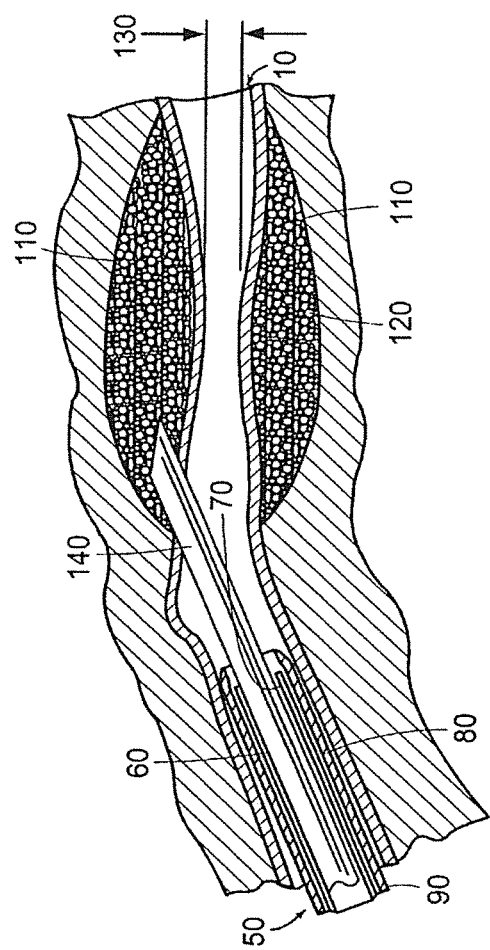
FIG. 3 depicts the tissue structure of FIG. 1 immediately after a bulking agent in accordance with the invention has been injected around the enlarged lumen of the tissue utilizing a cystoscope-aided injection method.

Alternatively, referring to FIG. 3, the urethra/ureter 10 is shown immediately after the bulking agent 110 of the present invention has been injected around the enlarged lumen 30 of the tissue 40 utilizing a cystoscope 50 aided injection method in accordance with another embodiment of the invention. An elongate needle 140 may be inserted through the working channel 70 into the urethra/ureter 10 and the surrounding tissue 40 and the injection can be completed operating solely through the cystoscope 50. This is generally the preferred method of operation on male patients for the area surrounding the urethra/ureter and is the preferred method for female patients for the area surrounding the ureter.

Furthermore, the present invention relates to a bulking agent including substantially spherical polyvinyl alcohol particles used to facilitate bulking in a region of the human body through injection of the particles into the treatment region. The particles are compliant enough to be delivered through a substantially small gauge injection device. In one embodiment, the particles are 50% compressible. This is accomplished through the use of particles that are adapted to compress as they pass through the small gauge injection device. In one embodiment, a 16 to 24 gauge needle is used to dispense the bulking composition without clogging. In other applications, other size needles may be preferred, for example 18-22 gauge.

Filling the space surrounding the urethra/ureter allows the sphincter to be more readily coapted by the patient to maintain continence. Generally, the present invention is employed in the treatment of diseases requiring bulking, e.g., urinary or fecal incontinence. Some examples of conditions that can be treated by way of the present invention include urinary incontinence, vesicourethral reflux, fecal incontinence and intrinsic sphincter deficiency or ISD. However, the bulking method described herein can also be used for soft tissue bulking for use during, for example, plastic surgery.

In greater detail, the method of providing a bulking agent to the human body includes using polymeric particles, such as polyvinyl alcohol, as a bulking agent and injecting the particles into the treatment region of the human body. An advantage of the present invention is that the particles are substantially non-biodegradable, thereby virtually eliminating the need for replenishing the particles to maintain efficacy. A further advantage of the present invention is that the substantially spherical size and shape of the particles allows for close packing of the particles in the treatment space.

In one embodiment, the particles are made of a water and polyvinyl alcohol mixture. For a description of particles contemplated for use with the present invention, see U.S. patent application Ser. Nos. 10/232,265, 10/215,594, 10/116,330, 10/109,966, 10/231,664, the disclosures of which are hereby incorporated by reference herein in their entirety. Generally, water, polyvinyl alcohol, and alginate are combined and pumped through a nozzle under pressure, generating substantially spherically-shaped droplets. The substantially spherically-shaped droplets encounter a solution that promotes cross-linking of the polyvinyl alcohol. Subsequently, the alginate is removed from the outer surface. The result is a substantially spherically-shaped particle that is substantially all polyvinyl alcohol.

To facilitate other treatments, dosages of bio-active agents can be added to the particles. For example, substances, such as drugs, growth factors, proteins, genes, and chemo-therapeutic agents can be added to the particles to enhance localized treatments while still providing significant bulking benefits. The particles themselves are substantially inert in that they do not tend to react with body fluids and/or tissue. For example, many other types of bulking particles swell in use. In contrast thereto, the substantially spherical polyvinyl alcohol particles are substantially dimensionally stable. Some tissue growth on, near, or around the particle surface may occur, but no biological interaction between the tissue and the particles is expected.

In one embodiment, the particles are substantially solid. In a particular embodiment, the particles are substantially spherically-shaped and are sized in a range of about 40 microns to about 1500 microns in diameter, preferably about 150 microns to about 1100 microns in diameter, and more preferably about 500 microns to about 900 microns in diameter. The size of the particles chosen for a particular application will be determined by a number of factors. Smaller particles are easier to inject with a smaller gauge size needle; however, embolization due to migration of the particles is a concern with the smaller particle sizes. The size of the particles used in a particular procedure will include consideration of the procedure employed, disease progression, the degree of degradation of the affected region, patient size, the disposition of the patient, and the preferences and techniques of the doctor performing the procedure. Similarly, such factors must be considered when determining the proper volume of bulking agent to inject into a patient. In one embodiment of the invention, the volume of bulking composition is about 1 ml to about 30 ml, and preferably about 20 ml to about 30 ml. In another embodiment, the volume of bulking composition injected into a patient is about 2 ml to about 16 ml. However, these amounts can vary significantly based on the doctor's determination as to when the target region is sufficiently bulked up.

To vary compressibility, provide for absorption of medications, or for the purpose of incorporating the particles into the surrounding tissue, the porosity of the particles may be modified. These effects, if desired, can be enhanced by increasing pore size. For example, tissue in-growth can be encouraged by increasing pore size. Preferably, pore sizes are within a range of about 4 microns to about 5 microns up to about 30 microns to about 50 microns. In one embodiment, the pores cover up to 80% of the surface area of the particle.

In one embodiment, the bulking particles are injected through a needle. In other embodiments, a cystoscope is used to allow for viewing the injection area. The bulking particles can be supplemented with a contrast agent to enhance their appearance as an aid to the doctor performing the procedure. Other methods of visual enhancement to assist in viewing of the bulking agent can also be employed. Injection of the particles can also be accomplished transuretherally by, for example, using a catheter.

In another embodiment, the method of providing the bulking agent to the human body further includes mixing the bulking particles with a carrier such that the particles are suspended in the carrier, and then injecting the particles-carrier mix into the treatment portion of the human body. The carrier serves as a lubricant for the particles thereby increasing the ease with which the particles move into the body. In another embodiment, the carrier is a saline solution. In other embodiments bio-compatible thickening agents such as alginate, beta-glucan, glycerin, cellulose, or collagen are added to the carrier or serve as the carrier themselves to modify the viscosity of the carrier. By varying the carrier viscosity, proper disbursement of the bulking particles can be accomplished; however, carriers must not be so viscous that their passage through an injection device is inhibited. In yet another embodiment, the carrier may be bio-active, that is the carrier includes an anti-microbial agent, or the like.

The present invention also relates to a method used to dilate tissue within a treatment tissue region to facilitate injection of the bulking agent. The method includes: inserting a needle with a penetration device (e.g., a taper point obtuator or trocar) into the treatment region (e.g., the sphincter region) (FIG. 4); removing the penetration device while retaining the inserted needle (FIG. 5); advancing a balloon through the needle (FIG. 6); inflating the balloon, thereby creating a void in the treatment region (FIG. 7); deflating and removing the balloon from the treatment region (FIG. 8); affixing a syringe with a bulking agent to the needle and injecting the bulking agent into the tissue void (FIG. 9). This procedure can be repeated as necessary in order to maximize the effectiveness of the bulking agent and to achieve the desired results.

Figure 4:
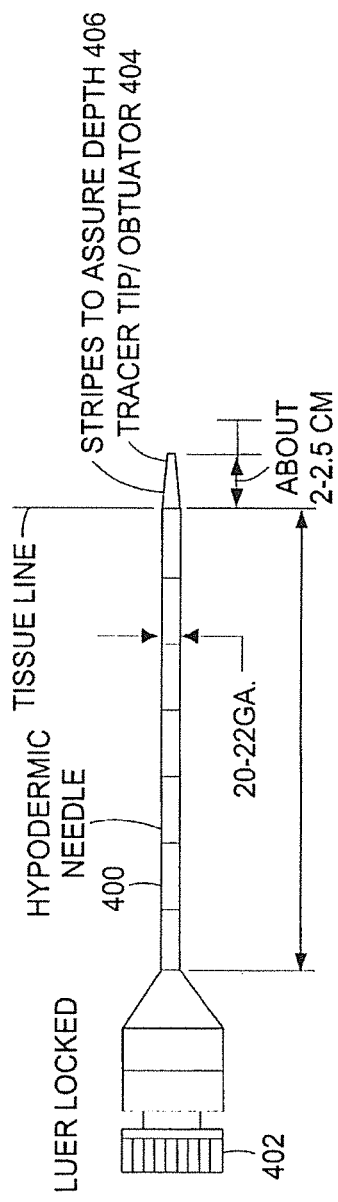
FIG. 4 is a schematic plan view of a needle assembly in accordance with the invention.
Figure 5:
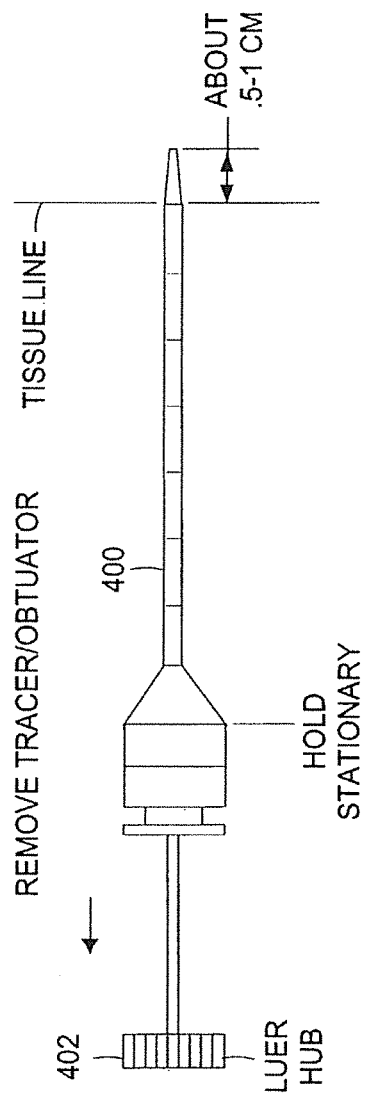
FIG. 5 is a schematic plan view of the needle assembly of FIG. 4 with the trocar/obtuator assembly being removed.

The method and apparatus for carrying out the method in a method to treat urinary incontinence by bulking the urethral tissue is described generally with reference to FIGS. 4-11. A needle 400, such as a blunt-end hypotube or hypodermic needle having a first end and a second end, is adapted to accept a penetration device 404, such as a taper point obtuator or a trocar, at the first end of the needle 400 (FIG. 4). The needle 400 may range in size from about 18 gauge to about 22 gauge, and preferably about 20 gauge to about 22 gauge. The penetration device 404 is attached to the needle 400 to enable penetration of the needle 400 into the tissue. The penetration device 404 may be adapted to the needle 400 by way of a luer hub or fitting, and in one embodiment, a male luer hub is used. The needle 400 is inserted with the penetration device 404 into the treatment region 420 (e.g., the sphincter region) (FIG. 10) to the desired depth. In one embodiment, desired penetration depth can be determined by striping 406 located on the penetration device 404. In one embodiment, the amount of penetration of the penetration device 404 ranges from about 2 cm to about 2.5 cm (FIG. 4). In one embodiment, the amount of tissue penetration of the needle 400 ranges from about 0.5 cm to about 1 cm beyond the tissue line, 407 (FIG. 5). The penetration device 404 is removed while retaining the inserted needle 400 (FIG. 6).

A luer hub 402 or fitting, or in one embodiment a female luer hub, may be adapted to the second end of the needle 400, to which a syringe 412, 418 (FIGS. 7-9) is adapted. Referring to FIG. 4, the luer hub 402 is depicted in its locked position, and in FIG. 5 the luer hub 402 is depicted in its unlocked position. In the locked position, the luer hub 402 can be positioned for inflating the balloon 408 or injecting a bulking agent 416. In the unlocked position, the luer hub 402 can be positioned for accepting the balloon 408 for insertion or for removal of the balloon 408 after dilation.

The balloon 408 is adapted to advance through a lumen of the needle 400, and an adapter on the balloon 408 provides a means to lock the balloon 408 to the luer hub 402, which in turn adapts to the syringe 412 (FIG. 6). The balloon 408 may have no tip or, alternatively, the balloon 408 may have a small stump appendage, which may remain from processing of the balloon. In one embodiment, the balloon 408 is affixed to an end of a plastic tube 410 (FIG. 6). In another embodiment, the tip for the balloon 408 is integral with a shaft. In yet another embodiment, balloon 408 includes at least one fill and/or evacuation port.

In one embodiment, the balloon is a colored balloon (e.g., blue) to facilitate remote visualization of the procedure and proper placement of the balloon. Alternatively, the balloon could be clear to transparent and the inflation media could be colored, for example, a colored saline solution. The balloon may be semi-compliant or non-compliant. The balloon may be manufactured from any suitable material, for example, a polymer. Some examples of suitable balloon materials include: silicone, ethylene vinyl acetate (EVA), polypropylene, latex rubber, polyurethane, polyester, nylon and thermoplastic rubber. In one embodiment, the balloon is inflated to, for example, about 3 cm to about 5 cm in diameter. The balloon may assume a variety of shapes. Some shapes that may be considered, depending upon the attendant requirements of the procedure, include substantially round, oval, hemi spherical, and oblong. The length of the balloon may vary depending upon the procedure. In one embodiment, the inflated balloon may have a length in the range of, for example, about 3 cm to about 10 cm. Other balloon configurations may be employed, and the types and methods used to employ the most suitable balloon configurations for a particular application of this invention will be obvious to those skilled in the art.

Figure 8:
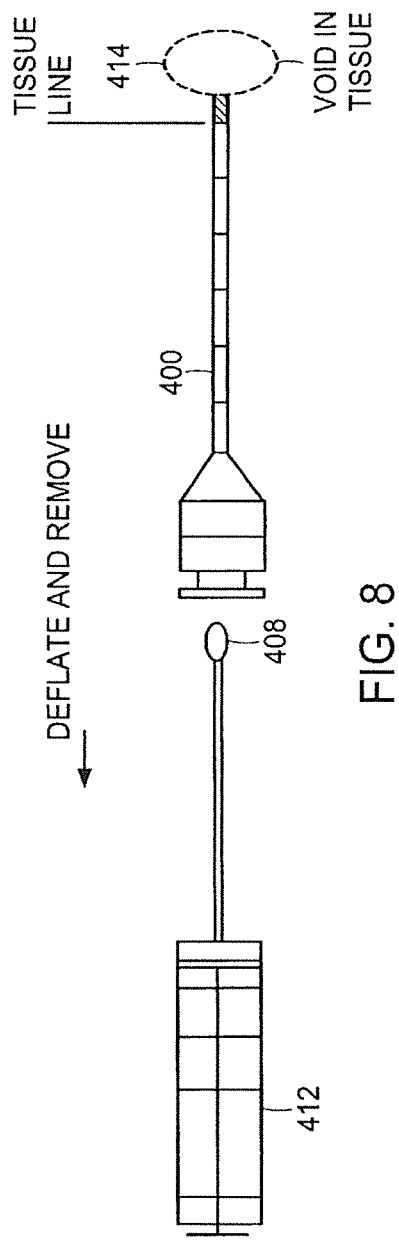
FIG. 8 is a schematic plan view of the assembly of FIG. 7 with the syringe and balloon assembly being removed.
Figure 9:
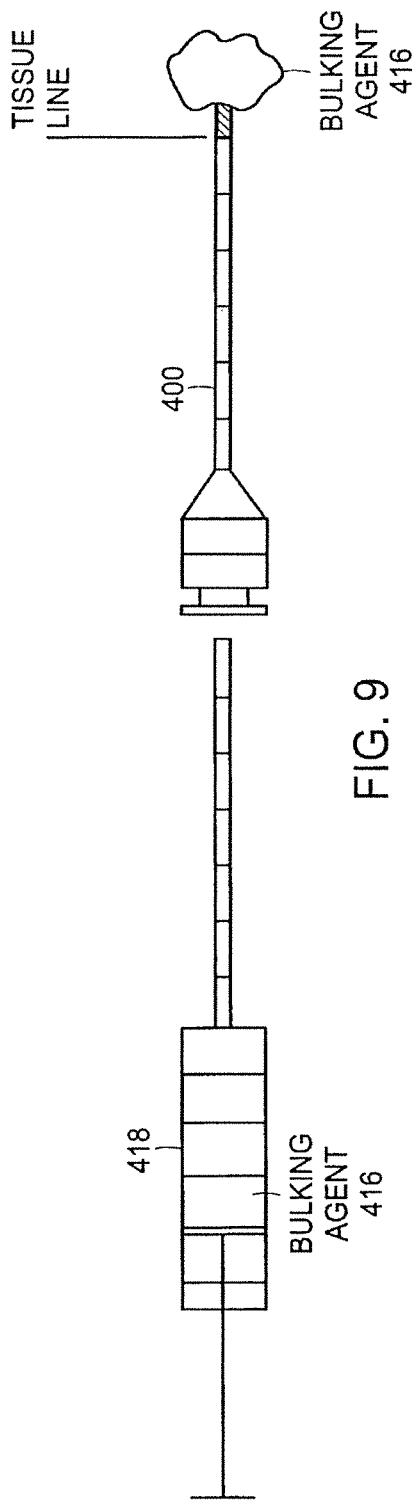
FIG. 9 is a schematic plan view of the assembly of FIG. 4 with another syringe attached to the needle assembly for injecting a bulking agent into tissue.

The balloon 408 is then inflated using an inflation device, such as the syringe 412, creating a void in the treatment region (FIGS. 7 and 8). The balloon may be colored (i.e. blue) to aid in visibility through the tissue. As the balloon 408 expands, the balloon 408 becomes visible to aid in proper balloon placement. For example, the expanding balloon 408 may become visible under the urethra as it thins. In one embodiment, the balloon 408 inflates to a volume of about ice to about 1.5 cc, although such volumes may vary depending upon many factors inherent in the characteristics of the particular application, some of which were discussed previously. In another embodiment, saline is used to inflate the balloon 408. In yet another embodiment, about 3 cc of saline is placed in the syringe 412 and injected into the balloon 408 for inflation.

Figure 10:
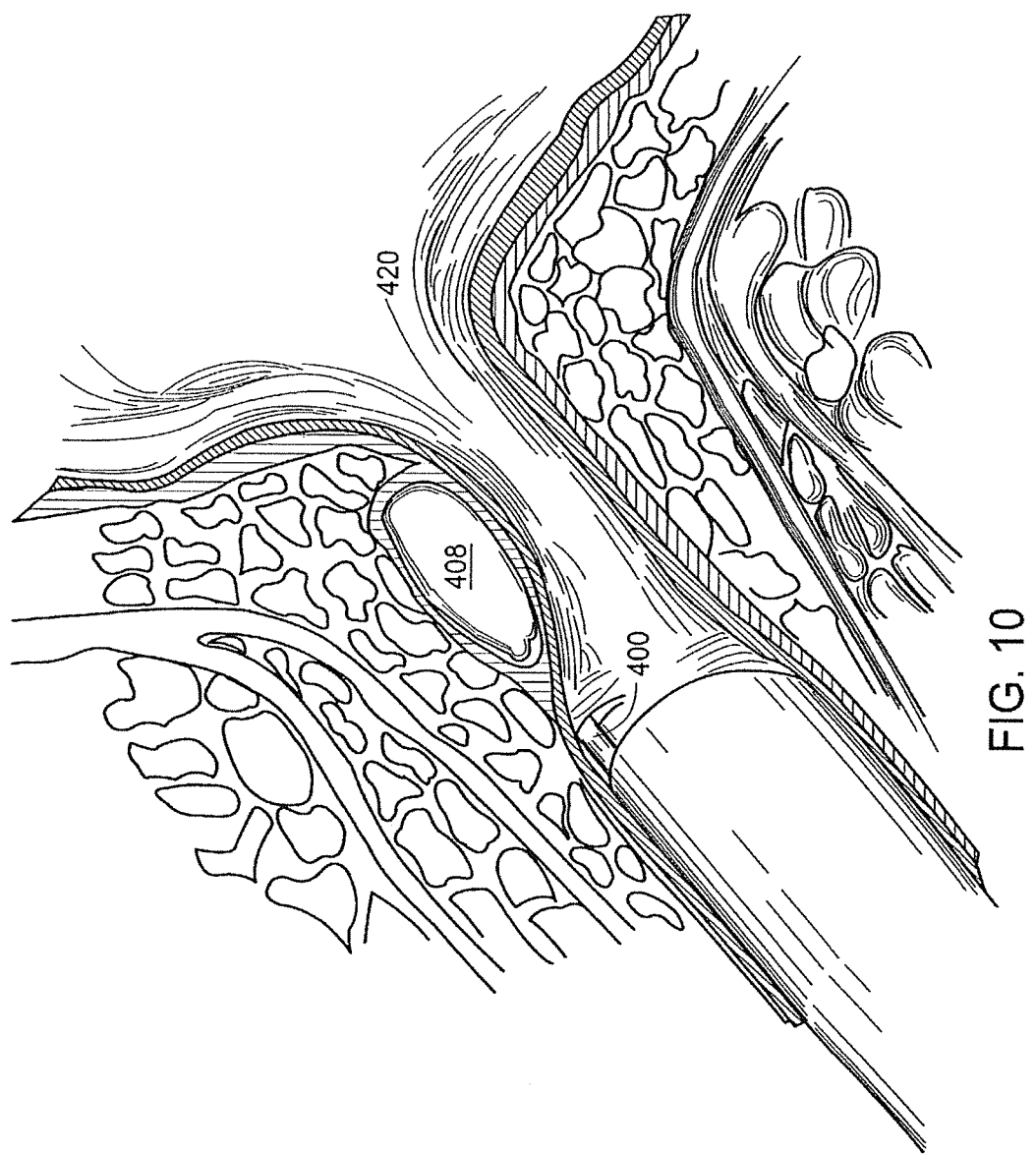
FIG. 10 is a pictorial representation of a method of creating a void within a patient's tissue by inserting and inflating a balloon.

The balloon 408 is then deflated and removed from the treatment region, resulting in a tissue void 414 where the inflated balloon 408 previously resided (FIGS. 8 and 10). The balloon 408 is removable through the lumen of the needle 400. In one embodiment, a plastic tube or other tip 410 is used to aid in removal of the balloon 408.

Figure 11:
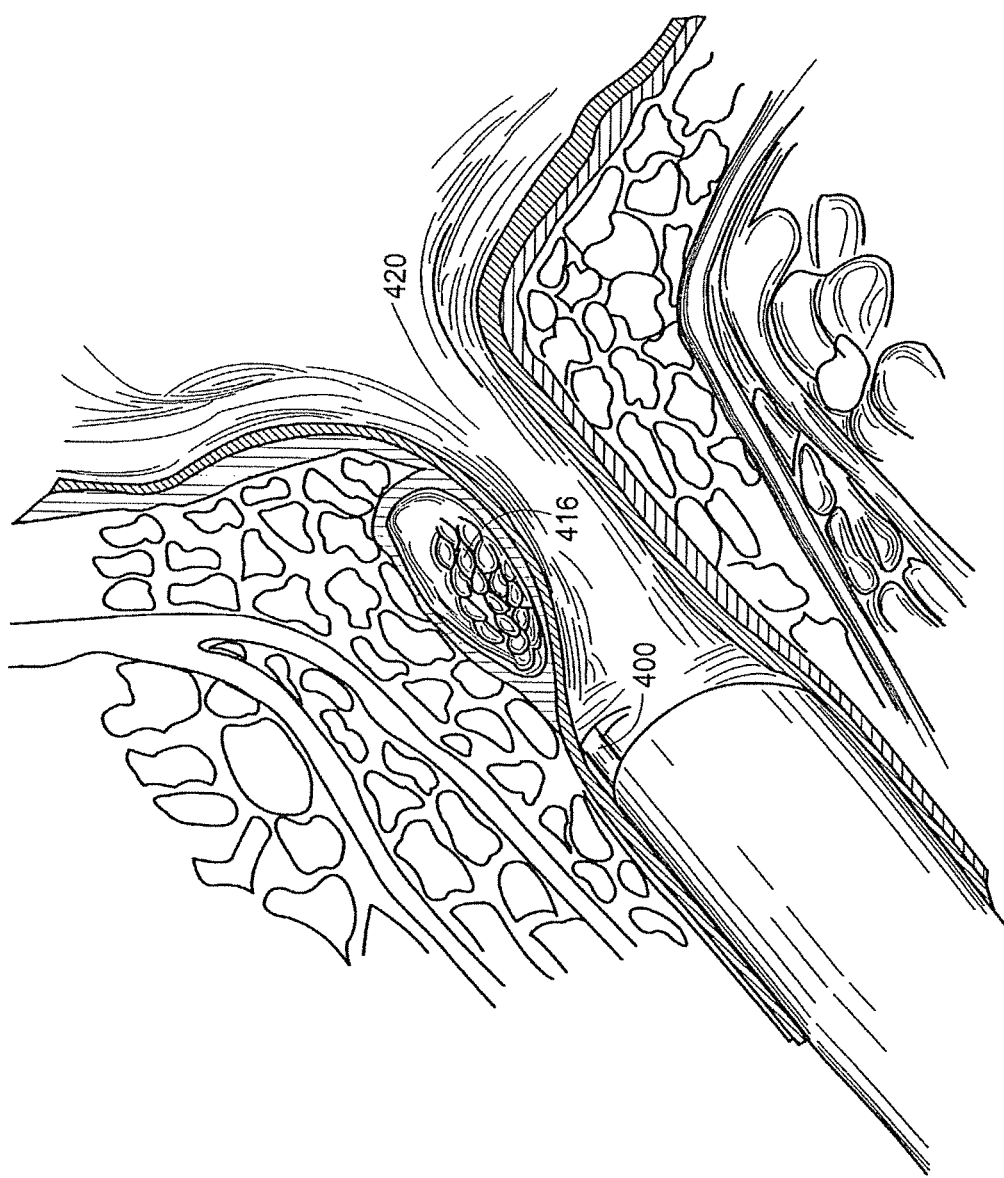
FIG. 11 is a pictorial representation of a method of filling the void within the patient's tissue with a bulking agent.

A syringe or other injection device 418 containing the bulking agent 416 is then affixed to the needle 400 by way of the luer hub 402. The plunger of the syringe 418 is then depressed, thereby injecting the bulking agent 416 into the tissue void 414 (FIGS. 9 and 11).

While the invention has been shown and described with reference to specific embodiments, it should be understood by those skilled in the art that various changes in form and detail may be made therein without departing from the spirit and scope of the invention.

Having thus described certain embodiments of the present invention, various alterations, modifications, and improvements will be apparent to those of ordinary skill. Such alterations, modifications, and improvements are within the spirit and scope of the invention, and the foregoing description of certain embodiments is not exhaustive or limiting.

What is claimed is:

1. A method for bulking mammalian tissue comprising the steps of:
   introducing a bulking agent to the mammalian tissue, the bulking agent comprising: a carrier, and a plurality of substantially spherical polyvinyl alcohol particles dispersed within the carrier, the substantially spherical polyvinyl alcohol particles comprising surface pores covering up to 80% of the total surface area of the particles and the carrier aiding delivery of the substantially spherical polyvinyl alcohol particles to a site to be bulked; and
   coapting the mammalian tissue with the substantially spherical polyvinyl alcohol particles.

2. The method of claim 1 further comprising the step of viewing the tissue to be bulked during the introducing step.

3. The method of claim 1 wherein the bulking agent comprises a volume from about 1 ml to about 30 ml.

4. The method of claim 1 wherein at least some of the substantially spherical polyvinyl alcohol particles are sized from about 40 microns to about 1500 microns in diameter.

5. The method of claim 1 wherein the substantially spherical polyvinyl alcohol particles comprise surface pores within a range of 4 to 50 microns.

6. The method of claim 1 wherein the substantially spherical polyvinyl alcohol particles comprise surface pores within a range of 5 to 30 microns.

7. The method of claim 1 wherein the substantially spherical polyvinyl alcohol particles are sized from 150 microns to 1100 microns in diameter.

8. The method of claim 1 wherein the substantially spherical polyvinyl alcohol particles are sized from 500 microns to 900 microns in diameter.

9. The method of claim 1 wherein the bulking agent is introduced into the mammalian tissue by through a needle.

10. The method of claim 9 wherein the needle is a 16 to 24 gauge needle.

11. The method of claim 9 wherein the needle is an 18 to 22 gauge needle.

12. The method of claim 1 wherein the substantially spherical polyvinyl alcohol particles comprise alginate.

13. The method of claim 1 wherein the bulking agent is delivered transurethrally to a urethra with a cystoscope comprising a light transmitting element, a working channel and a viewing element.

14. The method of claim 13 wherein the bulking agent is delivered by an elongate needle inserted through the working channel of the cystoscope.

15. The method of claim 1 wherein the bulking agent is injected around an enlarged lumen of a urethra.

16. The method of claim 1 wherein the bulking agent comprises a contrast agent.

17. A method for bulking mammalian tissue comprising:
   inserting an inflation device within a portion of a mammal;
   inflating the inflation device, thereby creating a void in the tissue; and
   at least partially filling the void with a bulking agent that comprises a carrier and a plurality of polymeric particles dispersed within the carrier, wherein the plurality of polymeric particles comprise surface pores covering up to 80% of the total surface area of the particles.

18. The method of claim 17, wherein the polymeric particles are sized in a range of about 40 microns to about 1500 microns in diameter.

19. The method of claim 18, wherein the polymeric particles comprise polyvinyl alcohol particles having surface pores.

20. The method of claim 12, wherein the substantially spherical polyvinyl alcohol particles are made by a process comprising:

forming substantially spherical droplets comprising polyvinyl alcohol and alginate;
crosslinking the polyvinyl alcohol in the substantially spherical droplets; and
subsequently removing alginate from an outer surface of the substantially spherical droplets to form substantially spherical particles that are substantially all polyvinyl alcohol.

\* \* \* \* \*